United States Patent
Elbe et al.

(10) Patent No.: US 6,992,098 B2
(45) Date of Patent: Jan. 31, 2006

(54) PYRAZOLYL BIPHENYL CARBOXAMIDES AND THE USE THEREOF FOR CONTROLLING UNDESIRED MICROORGANISMS

(75) Inventors: Hans-Ludwig Elbe, Wuppertal (DE); Heiko Rieck, Foy-lès-Lyon (FR); Ralf Dunkel, Monheim (DE); Ulrike Wachendorff-Neumann, Neuwied (DE); Astrid Mauler-Machnik, Leichlingen (DE); Karl-Heinz Kuck, Langenfeld (DE); Martin Kugler, Leichlingen (DE); Thomas Jaetsch, Köln (DE)

(73) Assignee: Bayer CropScience AG, Monheim (DE)

( * ) Notice: Subject to any disclaimer, the term of this patent is extended or adjusted under 35 U.S.C. 154(b) by 146 days.

(21) Appl. No.: 10/333,510

(22) PCT Filed: Jul. 11, 2001

(86) PCT No.: PCT/EP01/07990

§ 371 (c)(1),
(2), (4) Date: Jun. 18, 2003

(87) PCT Pub. No.: WO02/08195

PCT Pub. Date: Jan. 31, 2002

(65) Prior Publication Data

US 2004/0053971 A1 Mar. 18, 2004

(30) Foreign Application Priority Data

Jul. 24, 2000 (DE) .......................... 100 35 860
May 7, 2001 (DE) .......................... 101 22 097

(51) Int. Cl.
*A01N 31/56* (2006.01)
*C07D 231/14* (2006.01)

(52) U.S. Cl. ..................... 514/406; 548/374.1
(58) Field of Classification Search ................. 514/406; 548/374.1
See application file for complete search history.

(56) References Cited

U.S. PATENT DOCUMENTS

| | | | |
|---|---|---|---|
| 4,663,341 A | 5/1987 | Jacobson | 514/403 |
| 4,863,947 A | 9/1989 | Jacobson | 514/403 |
| 5,045,554 A | 9/1991 | Alt et al. | 514/365 |
| 5,080,708 A | 1/1992 | Freund et al. | 71/88 |
| 5,205,854 A | 4/1993 | Freund et al. | 504/191 |
| 5,223,526 A | 6/1993 | McLoughlin | 514/406 |
| 5,250,532 A | 10/1993 | McLaren et al. | 514/256 |
| 5,324,837 A | 6/1994 | Renga et al. | 544/33 |
| 5,330,995 A | 7/1994 | Eicken et al. | 514/355 |
| 5,416,103 A | 5/1995 | Eicken et al. | 514/355 |
| 5,438,070 A | 8/1995 | Eicken et al. | 514/403 |
| 5,480,897 A | 1/1996 | Eicken et al. | 514/365 |
| 5,556,988 A | 9/1996 | Eicken et al. | 548/374.1 |
| 5,589,493 A | 12/1996 | Eicken et al. | 514/355 |
| 5,763,450 A | 6/1998 | Guerry et al. | 514/275 |
| 6,147,104 A | 11/2000 | Eicken et al. | 514/406 |
| 6,369,093 B1 | 4/2002 | Elbe et al. | 514/406 |

FOREIGN PATENT DOCUMENTS

| | | |
|---|---|---|
| WO | 91/01311 | 2/1991 |
| WO | 92/00273 | 1/1992 |
| WO | 00/14071 | 3/2000 |

OTHER PUBLICATIONS

Synth. Commun., 30, (month unavailable) 2000, pp. 665–669, Pravin M. Bendale & Bhushan M. Khadilkar, "Silica Gel Supported Chromium Trioxide: An Efficient Reagent for Oxidative Cleavage or Oximes to Carbonyl Compounds Under Mild Condition".

Synth. Commun. 29, (month unavailable) 1999, pp. 1697–1701, Hajipour A.R., Mohammadpoor–Baltrok, I, Nikbaghat, K, and Imanzadeh, G., "Solid–Phase Synthesis of Oximes".

Database Crossfire Beilstein [Online] Beilstein Institut zur Förderung der Chemischen Wissenschaften, Frankfurt am Main, DE; dle Verbindung mit der BRN: 3118739, XP002179759 & Journal of Organic Chemistry., vol. 33, No. 12, 1968, pp. 4483–4486, American Chemical Society. Easton., US ISSN: 0022-3263.

*Primary Examiner*—Patricia L. Morris
(74) *Attorney, Agent, or Firm*—Richard E. L. Henderson; Raymond J. Harmuth

(57) ABSTRACT

Novel pyrazolylbiphenylcarboxamides of the formula (I)

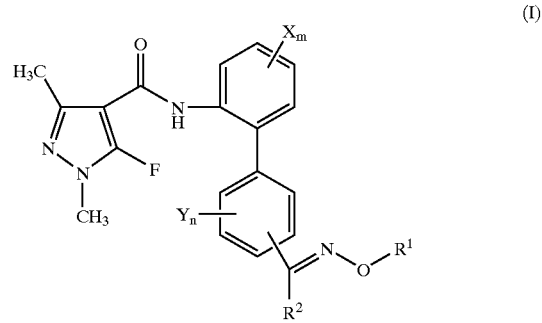

in which
R$^1$, R$^2$, X, m, Y and n are each as defined in the description,
a plurality of processes for preparing these substances and their use for controlling undesirable microorganisms, and also novel intermediates and their preparation.

6 Claims, No Drawings

PYRAZOLYL BIPHENYL CARBOXAMIDES AND THE USE THEREOF FOR CONTROLLING UNDESIRED MICROORGANISMS

The present invention relates to novel pyrazolylbiphenylcarboxamides, to a plurality of processes for their preparation and to their use for controlling undesirable microorganisms.

It is already known that numerous carboxanilides have fungicidal properties (compare WO 93/11 117, EP-A 0 545 099, EP-A 0 589 301, WO 99/09013, DE 198 40 322). Thus, N-(2-cyclohexyl)-1,3-dimethyl-5-fluoropyrazole-4-carboxanilide, N-(2-phenyl)-1,3-dimethyl-pyrazole-4-carboxanilide and N-2[2-(2-fluoro-phenyl)]-1,3-dimethyl-pyrazole-4-carboxanilide can be employed for controlling fungi. The activity of these substances is good; however, in some cases it is unsatisfactory at low application rates.

This invention, accordingly, provides novel pyrazolylbiphenylcarboxamides of the formula (I)

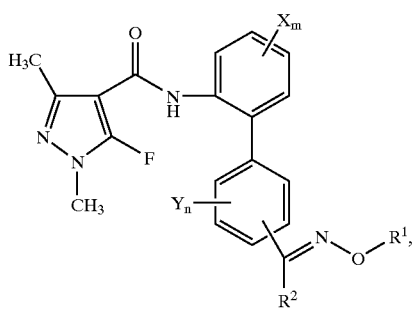

(I)

in which $R^1$ represents hydrogen, $C_1$–$C_6$-alkyl, $C_1$–$C_6$-halogenoalkyl, benzyl or pyridylmethyl, $R^2$ represents hydrogen or $C_1$–$C_6$-alkyl, X represents halogen, nitro, cyano, hydroxyl, carboxyl, $C_1$–$C_8$-alkyl, $C_1$–$C_6$-halogenoalkyl having 1 to 5 halogen atoms, $C_1$–$C_8$-alkoxy, $C_1$–$C_6$-halogenoalkoxy having 1 to 5 halogen atoms, $C_1$–$C_8$-alkylthio, $C_1$–$C_6$-halogenoalkylthio having 1 to 5 halogen atoms, $C_2$–$C_8$-alkenyloxy, $C_2$–$C_8$-alkinyloxy, $C_3$–$C_8$-cycloalkyl, $C_1$–$C_8$-alkoxycarbonyl or represents —C($R^2$)=N—O$R^1$, m represents integers from 0 to 3, where X represents identical or different radicals if m represents 2 or 3, Y represents halogen, nitro, cyano, hydroxyl, carboxyl, $C_1$–$C_8$-alkyl, $C_1$–$C_6$-halogenoalkyl having 1 to 5 halogen atoms, $C_1$–$C_8$-alkoxy, $C_1$–$C_6$-halogenoalkoxy having 1 to 5 halogen atoms, $C_1$–$C_8$-alkylthio, $C_1$–$C_6$-halogenoalkylthio having 1 to 5 halogen atoms, $C_2$–$C_8$-alkenyloxy, $C_2$–$C_8$-alkinyloxy, $C_3$–$C_8$-cycloalkyl, $C_1$–$C_8$-alkoxycarbonyl or $C_1$–$C_6$-alkoximino-$C_1$–$C_6$-alkyl and n represents integers from 0 to 4, where Y represents identical or different radicals if n represents 2, 3 or 4.

Furthermore, it has been found that pyrazolylbiphenyl-carboxamides of the formula (I) are obtained when a) carboxylic acid derivatives of the formula (II)

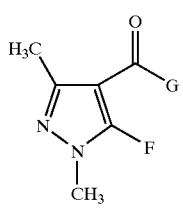

(II)

in which

G represents halogen, hydroxyl or $C_1$–$C_6$-alkoxy, are reacted with aniline derivatives of the formula (III)

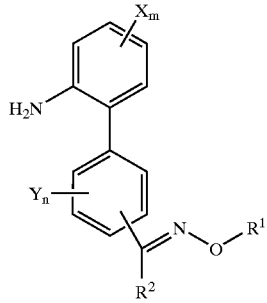

(III)

in which $R^1$, $R^2$, X, m, Y and n are each as defined above, if appropriate in the presence of a catalyst, if appropriate in the presence of an acid binder and if appropriate in the presence of a diluent, or b) carboxamide derivatives of the formula (IV)

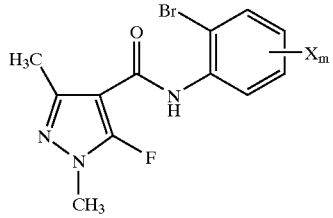

(IV)

in which

X and m are each as defined above, are reacted with boronic acid derivatives of the formula (V)

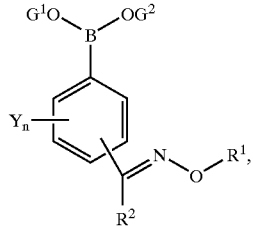

(V)

in which $R^1$, $R^2$, Y and n are each as defined above and $G^1$ and $G^2$ each represent hydrogen or together represent tetramethylethylene, if appropriate in the presence of a catalyst, if appropriate in the presence of an acid binder and if appropriate in the presence of a diluent, or c) carboxamide-boronic acid derivatives of the formula (VI)

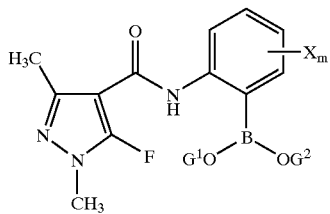
(VI)

in which

X and m are each as defined above and $G^1$ and $G^2$ each represent hydrogen or together represent tetramethylethylene, are reacted with phenyloxime derivatives of the formula (VII)

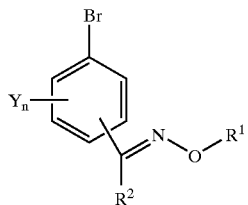
(VII)

in which $R^1$, $R^2$, Y and n are each as defined above, if appropriate in the presence of a catalyst, if appropriate in the presence of an acid binder and if appropriate in the presence of a diluent, or d) biphenylacyl derivatives of the formula (VIII)

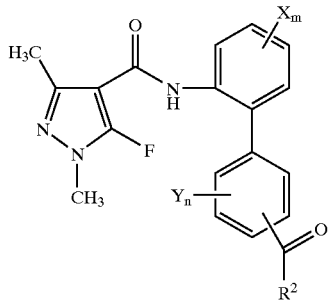
(VIII)

in which $R^2$, X, m, Y and n are each as defined above and are reacted with alkoxamines of the formula (IX)

$$R^1-O-NH_2 \cdot xHCl \quad (IX)$$

in which $R^1$ is as defined above, if appropriate in the presence of an acid binder and if appropriate in the presence of a diluent, or e) hydroxylamine derivatives of the formula (I-a)

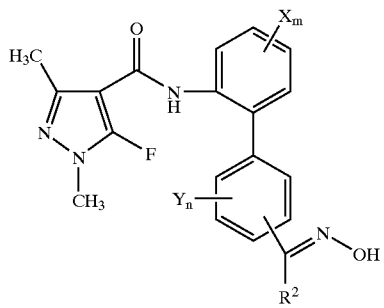
(I-a)

in which $R^2$, X, m, Y and n are each as defined above, are reacted with compounds of the formula (X)

$$R^3\text{-E} \quad (X)$$

in which $R^3$ represents $C_1$–$C_6$-alkyl and

E represents chlorine, bromine, iodine, methanesulphonyl or p-toluenesulphonyl, or $R^3$ and E together represent di-$C_1$–$C_6$-alkyl sulphate, if appropriate in the presence of an acid binder and if appropriate in the presence of a diluent, or f) carboxamide derivatives of the formula (IV)

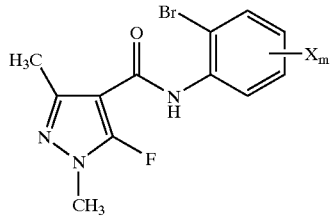
(IV)

in which

X and m are each as defined above, are reacted with phenyloxime derivatives of the formula (VII)

(VII)

Br $Y_n$ $N-O-R^1$ $R^2$ in which $R^1$, $R^2$, Y and n are each as defined above, in the presence of a palladium or platinum catalyst and in the presence of 4,4,4',4',5,5,5',5'-octamethyl-2,2'-bis-1,3,2-dioxaborolane, if appropriate in the presence of an acid binder and if appropriate in the presence of a diluent.

Finally, it has been found that the novel pyrazolylbiphenylcarboxamides of the formula (I) have very good microbicidal properties and can be used for controlling undesirable microorganisms both in crop protection and in the protection of materials.

Surprisingly, the pyrazolylbiphenylcarboxamides of the formula (I) according to the invention have considerably better fungicidal activity than the active prior-art compounds of the most similar constitution and the same direction of action.

The formula (I) provides a general definition of the pyrazolylbiphenylcarboxamides according to the invention.

$R^1$ preferably represents hydrogen, $C_1$–$C_4$-alkyl, $C_1$–$C_2$-halogenoalkyl having 1 to 5 fluorine, chlorine and/or bromine atoms, benzyl or pyridylmethyl.

$R^2$ preferably represents hydrogen or $C_1$–$C_4$-alkyl.

X preferably represents fluorine, chlorine, bromine, nitro, cyano, hydroxyl, carboxyl, $C_1$–$C_6$-alkyl, $C_1$–$C_2$-halogenoalkyl having 1 to 5 fluorine, chlorine and/or bromine atoms, $C_1$–$C_6$-alkoxy, $C_1$–$C_2$-halogenoalkoxy having 1 to 5 fluorine, chlorine and/or bromine atoms, $C_1$–$C_6$-alkylthio, $C_1$–$C_2$-halogenoalkylthio having 1 to 5 fluorine, chlorine and/or bromine atoms, $C_2$–$C_6$-alkenyloxy, $C_2$–$C_6$-alkinyloxy, $C_3$–$C_7$-cycloalkyl, $C_1$–$C_4$-alkoxycarbonyl or represents $C(R^2)=N-OR^1$.

m preferably represents integers from 0 to 3, where X represents identical or different radicals if m represents 2 or 3.

Y preferably represents fluorine, chlorine, bromine, nitro, cyano, hydroxyl, carboxyl, $C_1$–$C_6$-alkyl, $C_1$–$C_2$-halogenoalkyl having 1 to 5 fluorine, chlorine and/or bromine atoms, $C_1$–$C_6$-alkoxy, $C_1$–$C_2$-halogenoalkoxy having 1 to 5 fluorine, chlorine and/or bromine atoms, $C_1$–$C_6$-alkylthio, $C_1$–$C_2$-halogenoalkylthio having 1 to 5 fluorine, chlorine and/or bromine atoms, $C_2$–$C_6$-alkenyloxy, $C_2$–$C_6$-alkinyloxy, $C_3$–$C_7$-cycloalkyl, $C_1$–$C_4$-alkoxycarbonyl or $C_1$–$C_4$-alkoximino-$C_1$–$C_4$-alkyl.

n preferably represents integers from 0 to 3, where Y represents identical or different radicals if n represents 2 or 3.

$R^1$ particularly preferably represents hydrogen, methyl, ethyl, n-propyl, i-propyl, n-butyl, i-butyl, s-butyl, t-butyl, 2-chloroethyl, benzyl, 2-pyridylmethyl, 3-pyridylmethyl or 4-pyridylmethyl.

$R^2$ particularly preferably represents hydrogen, methyl, ethyl, n-propyl, i-propyl or n-butyl.

X particularly preferably represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, methylthio, trifluoromethylthio, difluorochloromethylthio, allyloxy, propargyloxy, cyclopropyl, cyclopentyl, cyclohexyl, cycloheptyl, methoxycarbonyl, ethoxycarbonyl or represents —$C(R^2)=N-OR^1$.

m particularly preferably represents integers from 0 to 2, where X represents identical or different radicals if m represents 2.

Y particularly preferably represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, methylthio, trifluoromethylthio, difluorochloromethylthio, allyloxy, propargyloxy, cyclopropyl, cyclopentyl, cyclohexyl, cycloheptyl, methoxycarbonyl, ethoxycarbonyl or methoximinomethyl.

n particularly preferably represents integers from 0 to 2, where Y represents identical or different radicals if n represents 2.

Preference is also given to compounds of the formula (I-b)

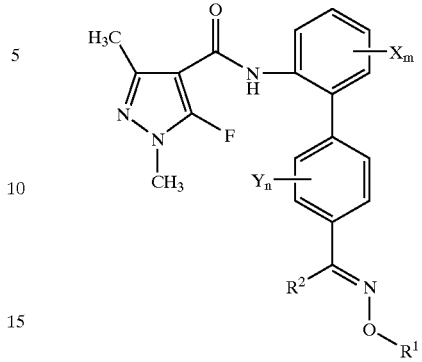

(I-b)

in which
$R^1$, $R^2$, X, m, Y and n are each as defined above.

Particular preference is given to compounds of the formula (I-b) in which $R^1$, $R^2$, X, m, Y and n have the meanings given above as being preferred or as being particularly preferred.

Preference is furthermore given to compounds of the formula (I-c)

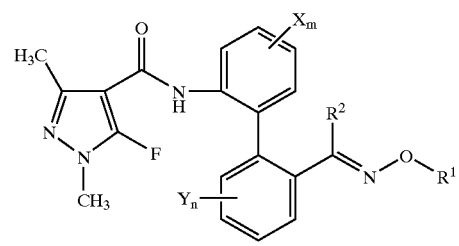

(I-c)

in which
$R^1$, $R^2$, X, m, Y and n are each as defined above.

Particular preference is given to compounds of the formula (I-c) in which $R^1$, $R^2$, X, m, Y and n have the meanings given above as being preferred or as being particularly preferred.

Preference is furthermore given to compounds of the formula (I-d)

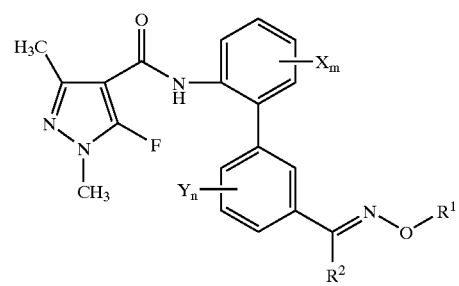

(I-d)

in which
$R^1$, $R^2$, X, m, Y and n are each as defined above.

Particular preference is given to compounds of the formula (I-d) in which $R^1$, $R^2$, X, m, Y and n have the meanings given above as being preferred or as being particularly preferred.

Preference or particular preference is given to compounds which carry the substituents mentioned under preferred or particularly preferred.

Saturated or unsaturated hydrocarbon radicals, such as alkyl or alkenyl, can in each case be straight-chain or branched as far as this is possible, including in combination with hetero atoms, such as, for example, in alkoxy.

Optionally substituted radicals can be mono- or polysubstituted, where in the case of polysubstitution the substituents can be identical or different. A plurality of radicals having the same indices, such as, for example, m radicals X for m>1, can be identical or different.

Halogen-substituted radicals, such as, for example, halogenoalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the abovementioned general or preferred radical definitions or illustrations can also be combined with one another as desired, i.e. including combinations between the respective ranges and preferred ranges. The definitions apply to the end products and, correspondingly, to the precursors and intermediates.

The abovementioned definitions can be combined with one another as desired. Moreover, individual definitions may not apply.

Using 1,3-dimethyl-5-fluoropyrazole-4-carbonyl chloride and 2-(4-methoximinomethyl-phenyl)aniline as starting materials, the course of the process (a) according to the invention can be illustrated by the equation below.

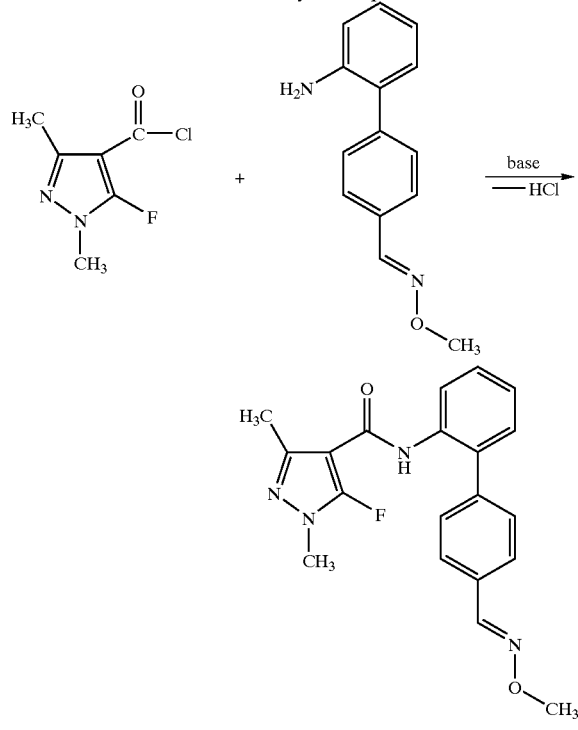

Using 2'-bromo-1,3-dimethyl-5-fluoropyrazol-4-carboxanilide and (4-methoximinomethyl)-phenylboronic acid as starting materials and a catalyst, the course of the process (b) according to the invention can be illustrated by the equation below.

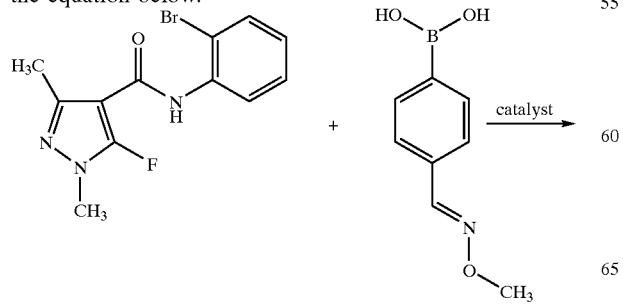

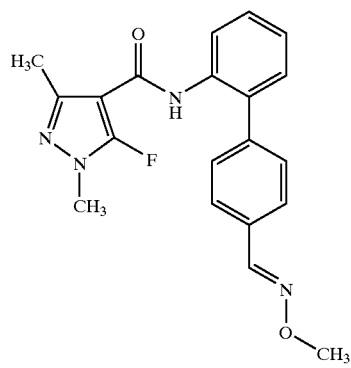

Using 2-[(1,3-dimethyl-5-fluoropyrazol-4-yl)carbonylamino]phenyl-boronic acid and 1-bromo-2-methoximinomethyl-benzene as starting materials and a catalyst, the course of the process (c) according to the invention can be illustrated by the equation below.

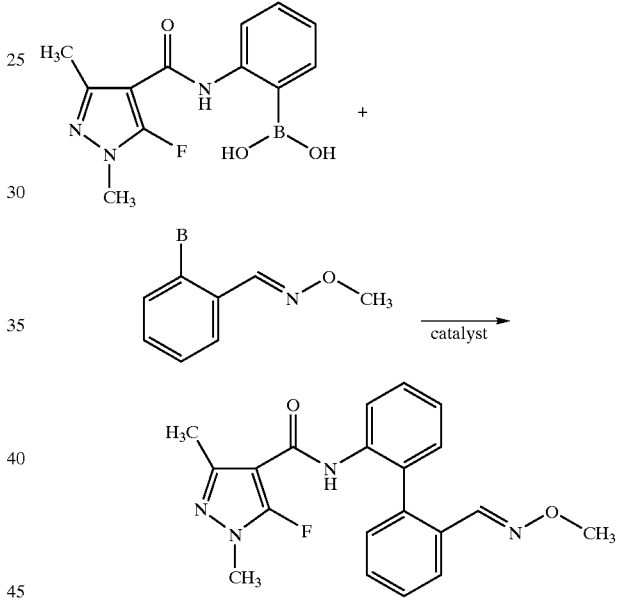

Using 2'-(4-acetyl-phenyl)-4'-fluoro-1,3-dimethyl-5-fluoropyrazole-4-carboxanilide and methoxamine hydrochloride as starting materials, the course of the process (d) according to the invention can be illustrated by the equation below.

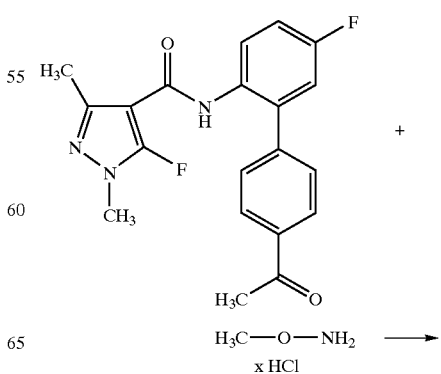

-continued

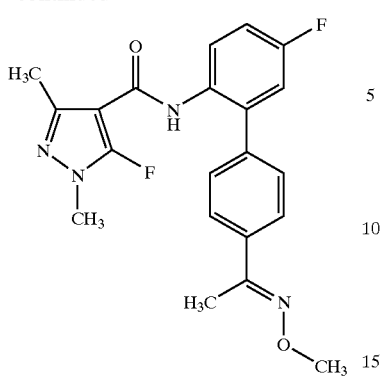

Using 2'-(4-hydroximinoethyl)-phenyl-1,3-dimethyl-5-fluoropyrazole-4-carboxanilide and methyl bromide as starting materials, the course of the process (e) according to the invention can be illustrated by the equation below.

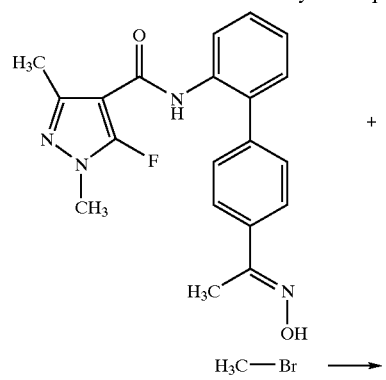

$H_3C{-}Br \longrightarrow$

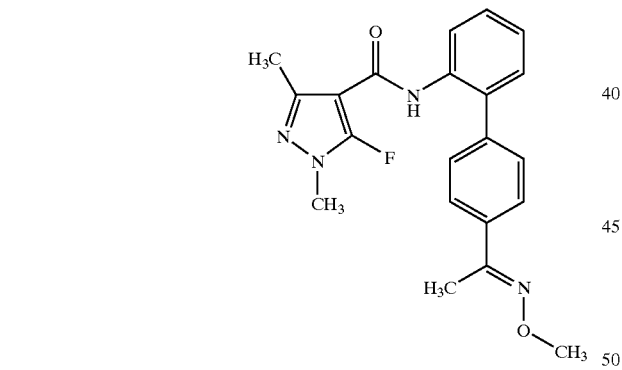

Using 2'-bromo-1,3-dimethyl-5-fluoropyrazole-4-carboxanilide and 1-bromo-4-methoximinomethyl-benzene as starting materials and a catalyst and 4,4,4',4',5,5,5',5'-octamethyl-2,2'-bis-1,3,2-dioxaborolane, the course of the process (f) according to the invention can be illustrated by the equation below.

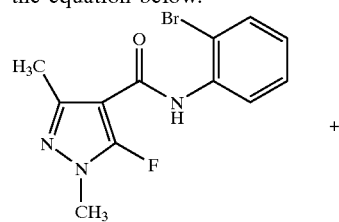

-continued

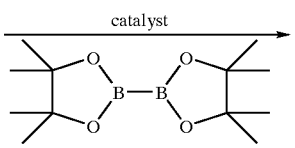

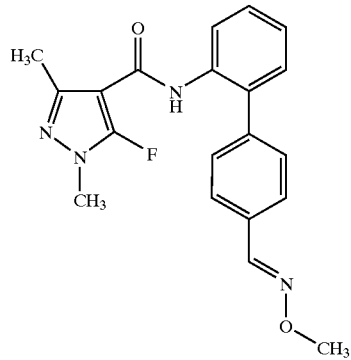

Illustration of the Processes and Intermediates

The formula (II) provides a general definition of the carboxylic acid derivatives required as starting materials for carrying out the process (a) according to the invention. In this formula, G preferably represents chlorine, bromine, hydroxyl, methoxy or ethoxy, particularly preferably chlorine, hydroxyl or methoxy.

The carboxylic acid derivatives of the formula (II) are known or can be prepared by known processes (cf. WO 93/11 117, EP-A 0 545 099, EP-A 0 589 301 and EP-A 0 589 313).

The formula (III) provides a general definition of the aniline derivatives required as reaction components for carrying out the process (a) according to the invention. In this formula, $R^1$, $R^2$, X, m, Y and n each preferably have those meanings which have already been mentioned in connection with the description of the substances of the formula (I) according to the invention as being preferred or being particularly preferred for these radicals or indices.

The aniline derivatives of the formula (III) are novel. Some of them can be prepared by known methods (cf. EP-A 0 545 099 and EP-A 0 589 301).

The aniline derivatives of the formula (III) are furthermore obtained by g) reacting 2-halogenoaniline derivatives of the general formula (XI)

(XI)

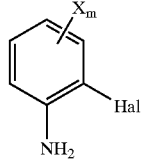

in which

X and m are each as defined above and

Hal represents halogen, with boronic acid derivatives of the formula (V)

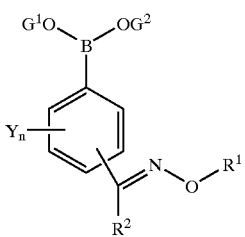

(V)

in which $R^1$, $R^2$, Y, n, $G^1$ and $G^2$ are each as defined above, if appropriate in the presence of an acid binder, and if appropriate in the presence of an inert organic diluent, and if appropriate in the presence of a catalyst, or h) by reacting anilineboronic acids of the formula (XII)

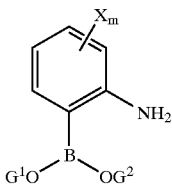

(XII)

in which
X, m, $G^1$ and $G^2$ are each as defined above
with phenyloxime derivatives of the formula (VII)

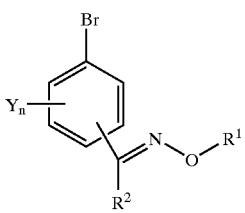

(VII)

in which $R^1$, $R^2$, Y and n are each as defined above, if appropriate in the presence of an acid binder, and if appropriate in the presence of an inert organic diluent, and if appropriate in the presence of a catalyst.

The formula (XI) provides a general definition of the 2-halogenoaniline derivatives required as reaction components for carrying out the process (g) according to the invention. In this formula, X and m each preferably have those meanings which have already been mentioned in connection with the description of the substances of the formula (I) according to the invention as being preferred or as being particularly preferred for these radicals or these indices. Hal preferably represents fluorine, chlorine or bromine, in particular chlorine or bromine.

The 2-halogenoaniline derivatives of the formula (XI) are commercially available or can be prepared from the corresponding nitro compounds by reduction.

The formula (XII) provides a general definition of the anilineboronic acids required as reaction components for carrying out the process (h) according to the invention. In this formula, X and m each preferably have those meanings which have already been mentioned in connection with the description of the substances of the formula (I) according to the invention as being preferred or as being particularly preferred for these radicals or these indices. $G^1$ and $G^2$ preferably each represent hydrogen or together represent tetramethylethylene.

The anilineboronic acids of the formula (XII) are commercially available.

The formula (IV) provides a general definition of the carboxamide derivatives required as starting materials for carrying out the processes (b) and (f) according to the invention. In this formula, X and m each preferably have those meanings which have already been mentioned in connection with the description of the substances of the formula (I) according to the invention as being preferred or as being particularly preferred for these radicals.

The carboxamide derivatives of the formula (IV) are known or can be prepared by known processes (cf. WO 91/01311, EP-A 0 371 950).

The formula (V) provides a general definition of the boronic acid derivatives required as reaction components when carrying out the process (b) and the process (g) according to the invention. In this formula, $R^1$, $R^2$, Y and n each preferably have those meanings which have already been mentioned in connection with the description of the substances of the formula (I) according to the invention as being preferred or as being particularly preferred for these radicals or these indices.

The boronic acid derivatives of the formula (V) are novel and can be prepared by i) reacting phenylboronic acids of the formula (XIII)

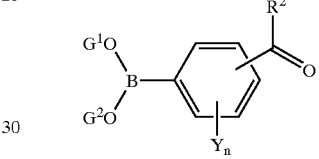

(XIII)

in which
$R^2$, Y, n, $G^1$ and $G^2$ are each as defined above,
with alkoxamines of the formula (IX)

$$R^1\text{—O—NH}_2 x\text{HCl}$$ (IX)

in which
$R^1$ is as defined above, if appropriate in the presence of an acid binder, and if appropriate in the presence of an inert organic diluent, and if appropriate in the presence of a catalyst.

The formula (XIII) provides a general definition of the phenylboronic acids required as reaction components for carrying out the process (h) according to the invention. In this formula, $R^2$, Y and n each preferably have those meanings which have already been mentioned in connection with the description of the substances of the formula (I) according to the invention as being preferred or as being particularly preferred for these radicals or these indices. $G^1$ and $G^2$ preferably each represent hydrogen or together represent tetramethylethylene.

The phenylboronic acids of the formula (XIII) are commercially available.

The formula (VI) provides a general definition of the carboxamide-boronic acid derivatives required as reaction components for carrying out the process (c) according to the invention. In this formula, X and m each preferably have those meanings which have already been mentioned in connection with the description of the substances of the formula (I) according to the invention as being preferred or as being particularly preferred for these radicals. $G^1$ and $G^2$ preferably each represent hydrogen or together represent tetramethylethylene.

The carboxamide-boronic acid derivatives of the formula (VI) are novel. They can be prepared by j) reacting carboxylic acid derivatives of the formula (II)

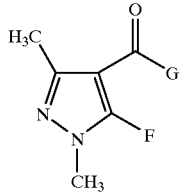
(II)

in which
G is as defined above,
with anilineboronic acids of the formula (XII)

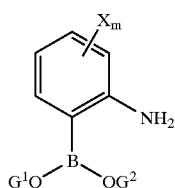
(XII)

in which
X, m, $G^1$ and $G^2$ are each as defined above,
if appropriate in the presence of an acid binder, and if appropriate in the presence of an inert organic diluent, and if appropriate in the presence of a catalyst.

The formula (VII) provides a general definition of the phenyloxime derivatives required as reaction components for carrying out the processes (c), (f) and (h) according to the invention. In this formula $R^1$, $R^2$, Y and n each preferably have those meanings which have already been mentioned in connection with the description of the substances of the formula (I) according to the invention as being preferred or as being particularly preferred for these radicals.

The phenyloxime derivatives of the formula (VII) are known or can be prepared by known processes (cf. Synth. Commun. 2000, 30, 665–669, Synth. Commun. 1999, 29, 1697–1701).

The formula (VIII) provides a general definition of the biphenylacyl derivatives required as starting materials for carrying out the process (d) according to the invention. In this formula, $R^2$, X, m, Y and n each have those meanings which have already been mentioned in connection with the description of the substances of the formula (I) according to the invention as being preferred or as being particularly preferred for these radicals.

The biphenylacyl derivatives of the formula (VIII) are novel. They can be prepared by k) reacting carboxylic acid derivatives of the formula (II)

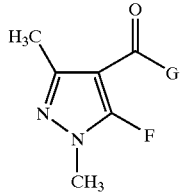
(II)

in which
G is as defined above,
with 2-benzaldehyde-aniline derivatives of the formula (XIV)

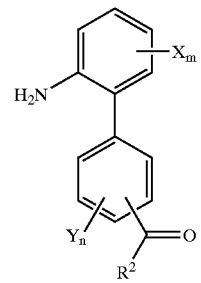
(XIV)

in which
$R^2$, X, m, Y and n are each as defined above,
if appropriate in the presence of an acid binder, and if appropriate in the presence of an inert organic diluent.

The formula (XIV) provides a general definition of the 2-benzaldehyde-aniline derivatives required as reaction components for carrying out the process (k) according to the invention. In this formula, $R^2$, X, m, Y and n each preferably have those meanings which have already been mentioned in connection with the description of the substances of the formula (I) according to the invention as being preferred or as being particularly preferred for these radicals.

The 2-benzaldehyde-aniline derivatives of the formula (XIV) are novel. They can be prepared by l) reacting aniline derivatives of the formula (XI)

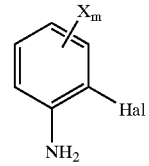
(XI)

in which
X and m are each as defined above and
Hal represents halogen,
with phenylboronic acid derivatives of the formula (XIII)

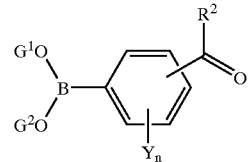
(XIII)

in which
$R^2$, Y, n, $G^1$ and $G^2$ are each as defined above,
if appropriate in the presence of an acid binder, and if appropriate in the presence of an inert organic diluent.

The formula (IX) provides a general definition of the alkoxamines required as reaction components for carrying out the process (d) according to the invention and the process (i). In this formula, $R^1$ preferably has those meanings which have already been mentioned in connection with the description of the substances of the formula (I) according to the invention as being preferred or as being particularly preferred for this radical. Preference is given to using the hydrochlorides mentioned in the description. However, it is also possible to use the free alkoxamines for the process according to the invention.

The alkoxamines of the formula (IX) are commercially available.

The formula (I-a) provides a general definition of the hydroxylamine derivatives required as starting materials for carrying out the process (e) according to the invention. In this formula, $R^2$, X, m, Y and n each preferably have those meanings which have already been mentioned in connection with the description of the substances of the formula (I) according to the invention as being preferred or as being particularly preferred for these radicals.

The hydroxylamine derivatives of the formula (I-a) according to the invention are novel. They can be prepared by one of the processes (a), (b), (c), (d) or (f) according to the invention described above.

The formula (X) provides a general definition of the compounds required as reaction components for carrying out the process (e) according to the invention. In this formula $R^3$ preferably represents $C_1$–$C_4$-alkyl, in particular methyl, ethyl, n-propyl, i-propyl or n-butyl. E preferably represents chlorine, bromine, iodine, methanesulphonyl or p-toluenesulphonyl. E particularly preferably represents chlorine or bromine.

The compounds of the formula (X) are commercially available.

Suitable acid binders for carrying out the processes (a), (b), (c), (d), (e) and (f) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to work in the absence of an additional acid binder or to employ an excess of the amine component, so that it simultaneously acts as acid binder.

Suitable diluents for carrying out the processes (a), (b), (c), (d), (e) and (f) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulfones, such as sulfolane.

When carrying out the processes (a), (b), (c), (d), (e) and (f) according to the invention, the reaction temperatures can in each case be varied within a relatively wide range. In general, the processes are carried out at temperatures between 0° C. and 140° C., preferably between 10° C. and 120° C.

The processes (a), (b), (c), (d), (e) and (f) according to the invention are generally in each case carried out under atmospheric pressure. However, in each case, it is also possible to operate under elevated or reduced pressure.

When carrying out the process (a) according to the invention, in general 1 mol or else an excess of the aniline derivative of the formula (III) and from 1 to 3 mol of acid binder are employed per mole of acid halide of the formula (II). However, it is also possible to employ the reaction components in other ratios. Work-up is carried out by customary methods. In general, the reaction mixture is mixed with water and the organic phase is separated off and, after drying, concentrated under reduced pressure. The residue that remains can, if appropriate, be freed by customary methods, such as chromatography or recrystallization, from any impurities that may be present.

When carrying out the process (b) according to the invention, in general 1 mol or else an excess of the boronic acid derivative of the formula (V) and from 1 to 5 mol of acid binder are employed per mole of carboxamide of the formula (IV). However, it is also possible to employ the reaction components in other ratios. Work-up is carried out by customary methods. In general, the reaction mixture is mixed with water and the precipitate is separated off and dried. The residue that remains can, if appropriate, be freed by customary methods, such as chromatography or recrystallization, from any impurities that may be present.

When carrying out the process (c) according to the invention, in general 1 mol or else an excess of the phenyloxime derivative of the formula (VII) and from 1 to 10 mol of acid binder and from 0.5 to 5 mol percent of a catalyst are employed per mole of carboxamide-boronic acid derivative of the formula (VI). However, it is also possible to employ the reaction components in other ratios. Work-up is carried out by customary methods. In general, the reaction mixture is mixed with water and the precipitate is separated off and dried. The residue that remains can, if appropriate, be freed by customary methods, such as chromatography or recrystallization, from any impurities that may be present.

When carrying out the process (d) according to the invention, in general 1 mol or else an excess of the alkoxamine of the formula (IX) and from 1 to 5 mol of acid binder are employed per mole of biphenylacyl derivative of the formula (VIII). However, it is also possible to employ the reaction components in other ratios. Work-up is carried out by customary methods. In general, the reaction mixture is mixed with water and the precipitate is separated off, washed with water and diisopropyl ether and then dried. The residue that remains can, if appropriate, be freed by customary methods, such as chromatography or recrystallization, from any impurities that may be present.

When carrying out the process (e) according to the invention, in general 1 mol or else an excess of the reagent of the formula (X) and from 1 to 5 mol of acid binder are employed per mole of hydroxylamine derivative of the formula (I-a). However, it is also possible to employ the reaction components in other ratios. Work-up is carried out by customary methods. In general, the reaction mixture is mixed with water and the precipitate is separated off and dried. The residue that remains can, if appropriate, be freed by customary methods, such as chromatography or recrystallization, from any impurities that may be present.

When carrying out the process (f) according to the invention, in general 1 mol or else an excess of the phenyloxime derivative of the formula (VII) and from 1 to 5 mol of acid binder and 1 to 5 mol of a catalyst are employed per mole of carboxamide derivative of the formula (IV). However, it is also possible to employ the reaction components in other ratios. Work-up is carried out by customary methods. In general, the reaction mixture is mixed with water and the precipitate is separated off and dried. The residue that remains can, if appropriate, be freed by customary methods, such as chromatography or recrystallization, from any impurities that may be present.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae*;
Pseudomonas species, such as, for example, *Pseudomonas syringae* pv. *lachrymans*;
Erwinia species, such as, for example, *Erwinia amylovora*;
Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Bremia species, such as, for example, *Bremia lactucae*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: *Drechslera*, syn: *Helminthosporium*);
Cochliobolus species, such as, for example, *Cochliobolus sativus* (conidia form: *Drechslera*, syn: *Helminthosporium*);
Uromyces species, such as, for example, *Uromyces appendiculatus*;
Puccinia species, such as, for example, *Puccinia recondita*;
Sclerotinia species, such as, for example, *Sclerotinia sclerotiorum*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae*; and
Pseudocercosporella species, such as, for example, *Pseudocercosporella herpotrichoides*.

The fact that the active compounds are well tolerated by plants at the concentrations required for controlling plant diseases permits the treatment of above-ground parts of plants, of propagation stock and seeds, and of the soil.

The active compounds according to the invention can be employed particularly successfully for controlling diseases in viticulture and fruit and vegetable growing such as, for example, against Venturia, Botrytis, Sclerotinia, Rhizoctonia, Uncinula, Sphaerotheca, Podosphaera, Alternaria and Colletotrichum. Rice diseases, such as Pyricularia and Pelliculariaspecies, are likewise controlled with good results.

The active compounds according to the invention are also suitable for increasing the yield of crops. In addition, they show reduced toxicity and are well tolerated by plants.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*, and
Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:
Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazolecis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB), quinoxyfen
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo [2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaphorthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
elfusilanate, emamectin, empenthrin, endosulfan, Entomopfthora spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin, nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302
zeta-cypermethrin, zolaprofos
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N''-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, for example against *Candida* species, such as *Candida albicans, Candida glabrata, Epidermophyton* species, such as *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*.

The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The compositions used for protecting industrial materials comprise the active compounds generally in an amount of from 1 to 95%, preferably from 10 to 75%.

The use concentrations of the active compounds according to the invention depend on the nature and occurrence of the microorganisms to be controlled and on the composition of the material to be protected. The optimum amount employed can be determined by a series of tests. In general, the use concentrations are in the range from 0.001 to 5% by weight, preferably from 0.05 to 1.0% by weight, based on the material to be protected.

The activity and the activity spectrum of the active compounds to be used according to the invention in material protection, or the compositions, concentrates or quite generally formulations preparable therefrom can be increased by adding, if appropriate, further antimicrobially active compounds, fungicides, bactericides, herbicides, insecticides or other active compounds for widening the activity spectrum or obtaining particular effects, such as, for example, additional protection against insects. These mixtures may have a wider activity spectrum than the compounds according to the invention.

The preparation and the use of the active compounds according to the invention is shown in the examples below.

PREPARATION EXAMPLES

Example 1

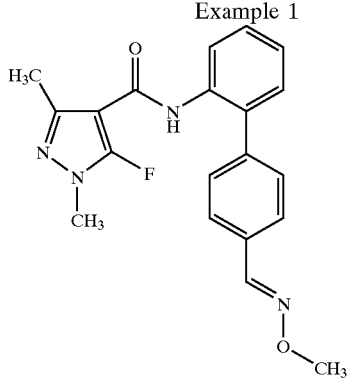

Process (a):

At room temperature, a solution of 1.3 g (0.0057 mol) of 2'-amino-1,1'-biphenyl-4-carbaldehyde O-methyloximine in 20 ml of toluene is admixed with 0.57 g (0.0057 mol) of triethylamine. At room temperature, a solution of 1.0 g (0.0057 mol) of 5-fluoro-1,3-dimethyl-1H-pyrazole-4-carbonyl chloride in 5 ml of toluene is added dropwise with stirring to this mixture. After the addition has ended, the reaction mixture is heated to 50° C. and stirred at this temperature for a further 2 h. For work-up, the reaction mixture is cooled to room temperature, mixed with another 25 ml of toluene and washed with water. The organic phase is separated off, dried over sodium sulphate, filtered and concentrated under reduced pressure. The residue that remains is recrystallized from diisopropyl ether. In this manner, 1.45 g (69.4% of theory) of 5-fluoro-N-{4'-[(methoxyimino)methyl]-1,1'-biphenyl-2-yl}-1,3-dimethyl-1H-pyrazole-4-carboxamide are obtained as colourless crystals of melting point 114 to 116° C.

Example 2

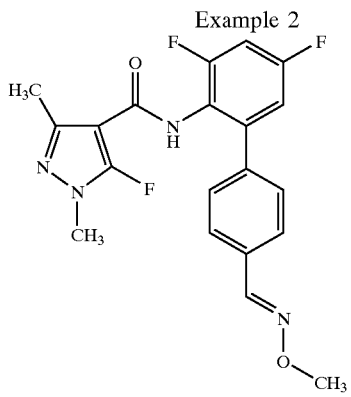

Process (b):

At room temperature, a mixture of 0.35 g (0.001 mol) of N-(2-bromo-4,6-difluorophenyl)-5-fluoro-1,3-dimethyl-1H-pyrazole-4-carboxamide, 0.06 g (0.00005 mol) of tetrakis-(triphenylphosphine)-palladium, 0.32 g (0.0018 mol) of 4-[(methoxyimino)methyl]phenylboronic acid and 10 ml of 1,2-dimethoxyethane is admixed with a solution of 0.5 g (0.0047 mol) of sodium carbonate in 3 ml of water. The reaction mixture is then heated to reflux temperature and kept at this temperature for 15 h. For work-up, the reaction mixture is stirred into 200 ml of water. The resulting precipitate is filtered off with suction and dried. The residue that remains is chromatographed on silica gel using the mobile phase cyclohexane:ethyl acetate=1:1. Concentration of the eluate gives 0.20 g (48% of theory) of N-{3,5-difluoro-4'-[(methoxyimino)methyl]-1,1'-biphenyl-2-yl}-5-fluoro-1,3-dimethyl-1H-pyrazole-4-carboxamide in the form of a solid of melting point 164 to 167° C.

Example 3

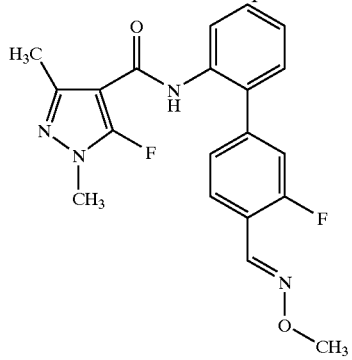

Process (c):

At room temperature, 1.28 g (12 mmol) of sodium carbonate, dissolved in 6 ml of water, are added to a mixture of 0.71 g (2 mmol) of 5-fluoro-1,3-dimethyl-N-[2-(4,4,5,5-tetramethyl-1,3,2-dioxaborolan-2-yl)phenyl]-1H-pyrazole-4-carboxamide, 1.39 g (6 mmol) of 4-bromo-2-fluorobenzaldehyde O-methyloxime, 0.03 g (0.05 mmol) of $PdCl_2$(dppf) and 40 ml of dimethyl sulphoxide. The reaction mixture is stirred at 80° C. for 15 hours.

For work-up, the reaction mixture is stirred into 400 ml of water and the precipitate is filtered off with suction and dried. The crude product is then purified by silica gel column chromatography using the mobile phase cyclohexane:ethyl acetate=1:1. Concentration gives 0.11 g (14% of theory) of 5-fluoro-N-{3'-fluoro-4'-[(methoxyimino)methyl]-1,1'-biphenyl-2-yl}-1,3-dimethyl-1H-pyrazole-4-carboxamide as crystals of melting point 158 to 161° C.

Example 4

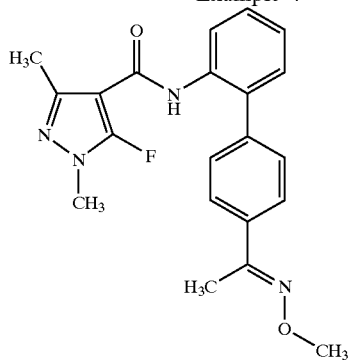

Process (d):

A mixture of 1.0 g (0.0028 mol) of N-(4'-acetyl-1,1'-biphenyl-2-yl)-5-fluoro-1,3-dimethyl-1H-pyrazole-4-carboxamide, 0.30 g (0.0036 mol) of O-methyl-hydroxylamine hydrochloride, 0.30 g (0.0036 mol) of sodium acetate and 6 ml of methanol is stirred at room temperature for 12 h. For work-up, the reaction mixture is stirred into water and the resulting precipitate is filtered off with suction, washed with water and then with a little diisopropyl ether and dried. This gives 0.91 g (85.4% of theory) of 5-fluoro-N-[4'-(N-methoxyethaneimidoyl)-1,1'-biphenyl-2-yl]-1,3-dimethyl-1H-pyrazole-4-carboxamide of melting point 153° C.

$^1$H-NMR spectrum (DMSO/TMS): δ=3.60 ppm.

Preparation of Starting Materials

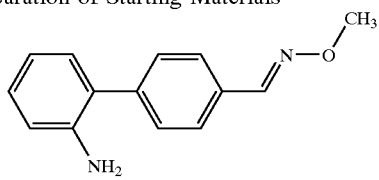

Process (g):

At room temperature, a mixture of 2.9 g (0.017 mol) of 2-bromoaniline, 0.68 g of tetrakis-(triphenylphosphine)-palladium, 5.5 g (0.031 mol) of 4-[(methoxyimino)methyl]phenylboronic acid and 40 ml of 1,2-dimethoxyethane is admixed with a solution of 8.2 g (0.077 mol) of sodium carbonate in 35 ml of water. The reaction mixture is then heated to reflux temperature and boiled for 12 h. For work-up, the mixture is cooled to room temperature and extracted with diethyl ether. The organic phase is separated off and admixed with water. The organic phase is again separated off, dried over sodium sulphate and finally concentrated under reduced pressure. The residue that remains is chromatographed on silica gel using the mobile phase cyclohexane:ethyl acetate=3:1. The eluate is concentrated, giving 3.8 g (98.8% of theory based on 2-bromoaniline) of 2'-amino-1,1'-biphenyl-4-carbaldehyde O-methyloxime in the form of an oil.

$^1$H-NMR spectrum (DMSO/TMS): δ=3.90 (3H) ppm.

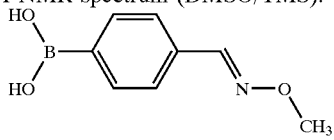

Process (i):

A mixture of 5.0 g (0.033 mol) of 4-formylphenylboronic acid, 3.4 g (0.041 mol) of O-methylhydroxylamine hydrochloride, 3.4 g (0.041 mol) of sodium acetate, 40 ml of methanol and 10 ml of water is stirred at room temperature for 12 h. For work-up, the reaction mixture is stirred with water and the resulting precipitate is filtered off with suction, washed with water and dried at 50° C. under reduced pressure. This gives 5.56 g (93.1% of theory) of 4-[(methoxyimino)methyl]phenylboronic acid as colourless crystals of melting point 199–200° C.

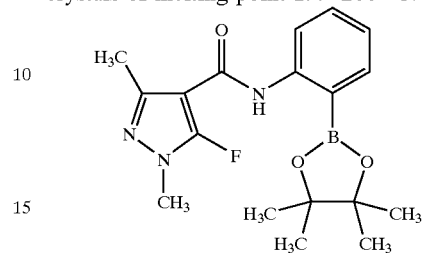

Process (j):

0.55 g (4 mmol) of potassium carbonate and 0.30 g (0.0017 mol) of 5-fluoro-1,3-dimethyl-1H-pyrazole-4-carbonyl chloride are, at room temperature, added to a mixture of 0.39 g (1.5 mmol) of 2-(4,4,5,5-tetramethyl-1,3,2-dioxaborolan-2-yl)aniline hydrochloride and 20 ml of acetonitrile. The reaction mixture is stirred at room temperature for 20 h.

For work-up, the reaction mixture is stirred into 150 ml of water and extracted with ethyl acetate, and the extract is dried over sodium sulphate. The organic phase is concentrated under reduced pressure and the solid residue is stirred with diisopropyl ether. This gives 0.25 g (46% of theory) of 5-fluoro-1,3-dimethyl-N-[2-(4,4,5,5-tetramethyl-1,3,2-dioxaborolan-2-yl)phenyl]-1H-pyrazole-4-carboxamide in the form of crystals of melting point 100–103° C.

The biphenylcarboxamides of the formula (I) listed in the table below are also prepared by the methods described above.

TABLE 1

| Ex. No. | Compound | Physical constant |
|---|---|---|
| 5 | ![compound 5] | m.p. 122–125° C. |
| 6 | ![compound 6] | m.p. 144–145° C. |

TABLE 1-continued

| Ex. No. | Compound | Physical constant |
|---|---|---|
| 7 | | logP 3.20[a)] |
| 8 | | logP 3.39[a)] |
| 9 | | logP 2.51[a)] |
| 10 | | logP 3.26[a)] |

TABLE 1-continued

| Ex. No. | Compound | Physical constant |
|---|---|---|
| 11 | | logP 3.05[a)] |
| 12 | | logP 1.75[a)] |
| 13 | | logP 4.02[a)] |
| 14 | | logP 3.68[b)] |

TABLE 1-continued

| Ex. No. | Compound | Physical constant |
|---|---|---|
| 15 | (structure) | logP 1.81[a)] |
| 16 | (structure) | logP 1.72[a)] |
| 17 | (structure) | logP 1.89[a)] |
| 18 | (structure) | logP 169[a)] |

TABLE 1-continued

| Ex. No. | Compound | Physical constant |
|---|---|---|
| 19 | (structure) | logP 1.60[a)] |
| 20 | (structure) | m.p. 115–117° C. |
| 21 | (structure) | m.p. 124–126° C. |
| 22 | (structure) | m.p. 115–117° C. |

TABLE 1-continued

| Ex. No. | Compound | Physical constant |
|---|---|---|
| 23 | (structure) | m.p. 115–117° C. |
| 24 | (structure) | m.p. 102–104° C. |
| 25 | (structure) | logP 3.38[a)] |
| 26 | (structure) | logP 3.40[a)] |

TABLE 1-continued

| Ex. No. | Compound | Physical constant |
|---|---|---|
| 27 | (structure) | logP 3.15[a] |
| 28 | (structure) | logP 3.67[a] |
| 29 | (structure) | logP 3.39[a] |
| 30 | (structure) | logP 3.27[a] |

TABLE 1-continued

| Ex. No. | Compound | Physical constant |
|---|---|---|
| 31 | | logP 3.34[a] |
| 32 | | logP 3.10[a] |
| 33 | | logP 3.79[a] |
| 34 | | logP 3.74[a] |

TABLE 1-continued
| Ex. No. | Compound | Physical constant |
|---|---|---|
| 35 | 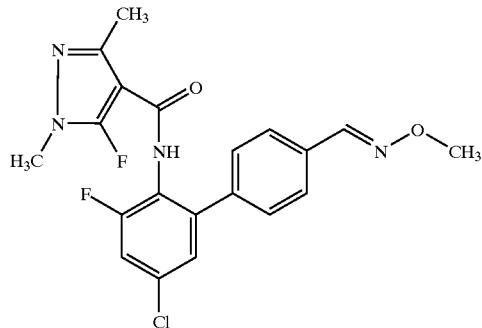 | logP 3.11[a] |
| 36 | 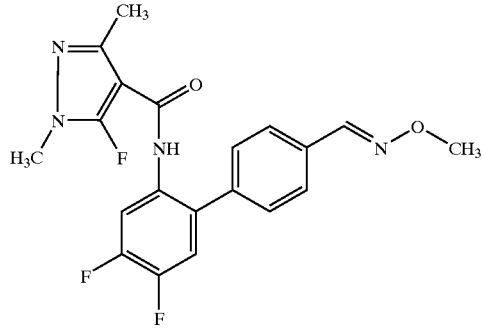 | logP 3.48[a] |
| 37 | 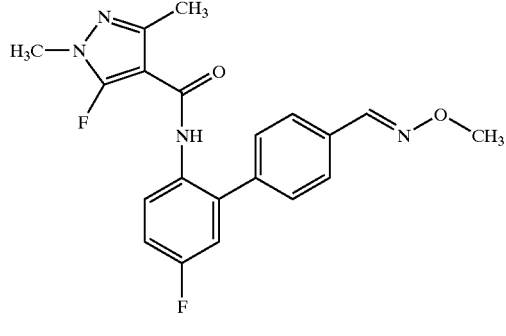 | logP 3.01[a] |
| 38 | 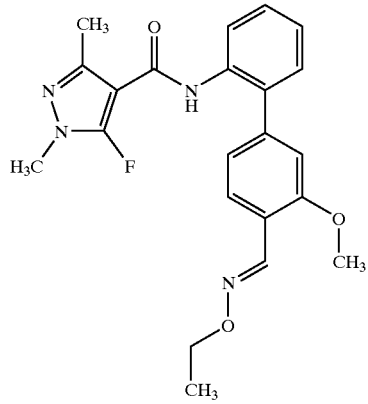 | logP 3.58[a] |

TABLE 1-continued

| Ex. No. | Compound | Physical constant |
|---|---|---|
| 39 | | logP 3.91[a)] |
| 40 | | logP 4.63[a)] |
| 41 | | logP 3.89[a)] |
| 42 | | logP 4.09[a)] |

TABLE 1-continued

| Ex. No. | Compound | Physical constant |
|---|---|---|
| 43 | (structure) | logP 4.06[a] |
| 44 | (structure) | logP 4.63[a] |
| 45 | (structure) | m.p. 147–149° C. |
| 46 | (structure) | logP 3.47[a] |

TABLE 1-continued

| Ex. No. | Compound | Physical constant |
|---|---|---|
| 47 | | logP 3.30[a] |
| 48 | | logP 3.25[a] |
| 49 | | |
| 50 | | logP 3.89[a] |

TABLE 1-continued
| Ex. No. | Compound | Physical constant |
|---|---|---|
| 51 | 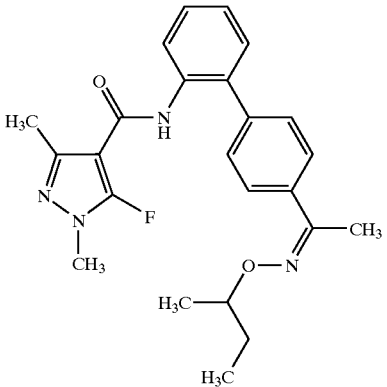 | logP 4.67[a)] |
| 52 | 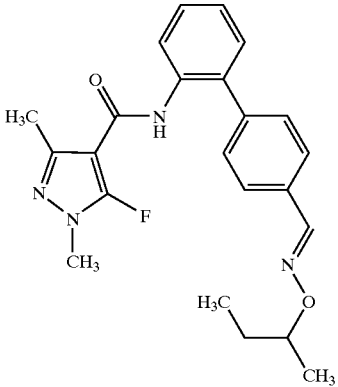 | |
| 53 | 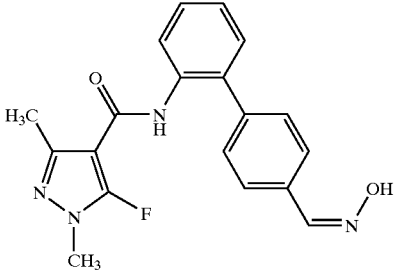 | logP 2.24[a)] |
| 54 | 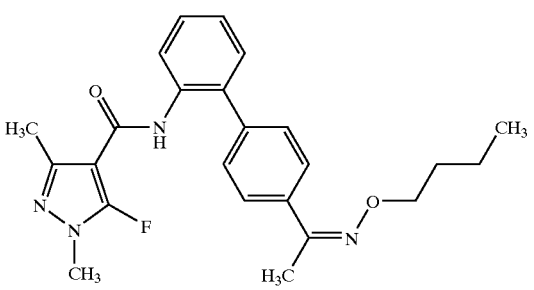 | m.p. 97–99° C. |

TABLE 1-continued

| Ex. No. | Compound | Physical constant |
|---|---|---|
| 55 | [Structure: pyrazole carboxamide with H3C, N-N-CH3, F substituents, connected via NH-C(=O) to biphenyl bearing CH=N-O-CH2CH2-R3] | logP 4.33[a)] |

The logP values given in the Preparation Examples and Tables above were determined in accordance with EEC Directive 79/831 Annex V.A8 by HPLC (High Performance Liquid Chromatography) on a reversed-phase column (C 18). Temperature: 43° C.

In the acidic range, the determination was carried out at pH 2.3 using the mobile phases 0.1% aqueous phosphoric acid and acetonitrile; linear gradient from 10% acetonitrile to 90% acetonitrile (marked [a)] in the Table).

In the neutral range, the determination was carried out at pH 7.5 using the mobile phases 0.01 molar aqueous phosphate buffer solution and acetonitrile; linear gradient from 10% acetonitrile to 90% acetonitrile (marked [b)] in the Table).

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Use Examples

Example A

*Podosphaera* Test (Apple)/Protective

| Solvents: | 24.5 parts by weight of acetone |
| | 24.5 parts by weight of dimethylacetamide |
| Emulsifier: | 1.0 part by weight of alkyl-aryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE A

Podosphaera test (apple)/protective

| Active compound | Application rate of active compound in g/ha | % efficacy |
|---|---|---|
| (I-1) [Structure: pyrazole carboxamide with H3C, N-N-CH3, connected via NH-C(=O) to biphenyl bearing CH=N-O-CH3] | 100 | 100 |

TABLE A-continued

Podosphaera test (apple)/protective

| Active compound | | Application rate of active compound in g/ha | % efficacy |
|---|---|---|---|
| (I-8) | [structure] | 100 | 98 |
| (I-11) | [structure] | 100 | 100 |
| (I-20) | [structure] | 100 | 95 |

TABLE A-continued
Podosphaera test (apple)/protective
| Active compound | Application rate of active compound in g/ha | % efficacy |
|---|---|---|
| (I-22) 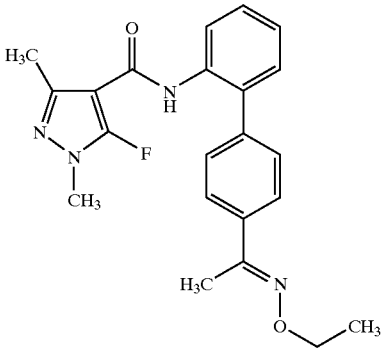 | 100 | 99 |
| (I-23) 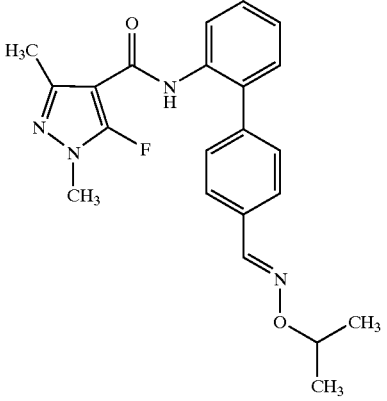 | 100 | 100 |
| (I-26) 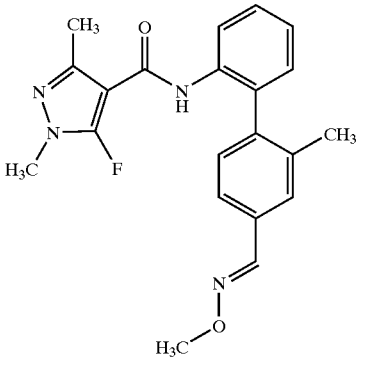 | 100 | 100 |
| (I-29) 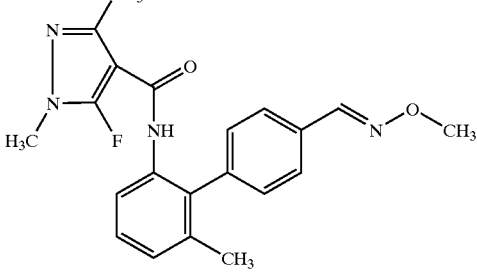 | 100 | 94 |

TABLE A-continued

Podosphaera test (apple)/protective

| Active compound | Application rate of active compound in g/ha | % efficacy |
|---|---|---|
| (I-37) | 100 | 100 |
| (I-39) | 100 | 100 |
| (I-46) | 100 | 100 |

TABLE A-continued

Podosphaera test (apple)/protective

| Active compound | Application rate of active compound in g/ha | % efficacy |
|---|---|---|
| (I-47) [structure] | 100 | 100 |
| (I-50) [structure] | 100 | 100 |

Example B

*Sphaerotheca* Test (Cucumber)/Protective

| Solvents: | 24.5 parts by weight of acetone |
| | 24.5 parts by weight of dimethylacetamide |
| Emulsifier: | 1.0 part by weight of alkyl-aryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE B

Sphaerotheca test (cucumber)/protective

| Active compound | | Application rate of active compound in g/ha | % efficacy |
|---|---|---|---|
| (I-1) | | 100 | 100 |
| (I-11) | | 100 | 93 |
| (I-20) | | 100 | 77 |

TABLE B-continued
Sphaerotheca test (cucumber)/protective
| Active compound | Application rate of active compound in g/ha | % efficacy |
|---|---|---|
| (I-22) 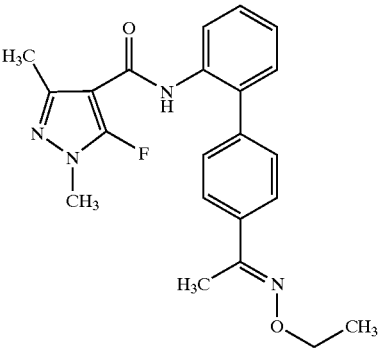 | 100 | 95 |
| (I-23) 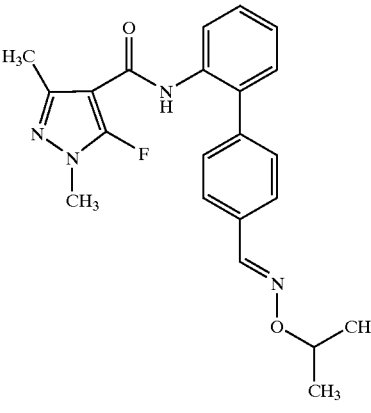 | 100 | 95 |
| (I-26) 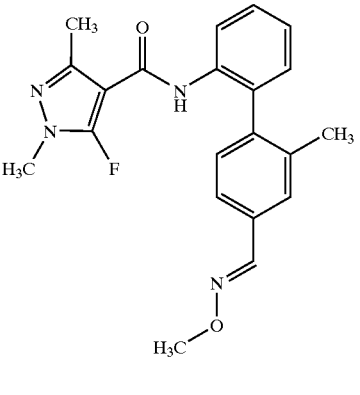 | 100 | 95 |
| (I-29) 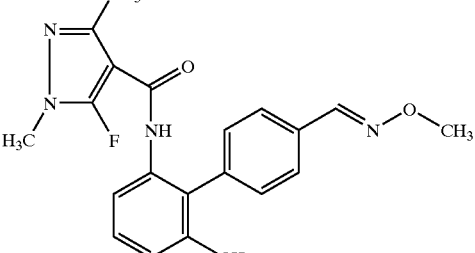 | 100 | 83 |

TABLE B-continued

Sphaerotheca test (cucumber)/protective

| Active compound | Application rate of active compound in g/ha | % efficacy |
|---|---|---|
| (I-37) | 100 | 77 |
| (I-39) | 100 | 97 |
| (I-46) | 100 | 100 |

TABLE B-continued

Sphaerotheca test (cucumber)/protective

| Active compound | Application rate of active compound in g/ha | % efficacy |
|---|---|---|
| (I-47) [structure] | 100 | 100 |
| (I-50) [structure] | 100 | 100 |

Example C

*Venturia* Test (Apple)/Protective

| Solvents: | 24.5 parts by weight of acetone |
|---|---|
| | 24.5 parts by weight of dimethylacetamide |
| Emulsifier: | 1.0 part by weight of alkyl-aryl polyglycol ether |

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE C

Venturia test (apple)/protective

| Active compound | | Application rate of active compound in g/ha | % efficacy |
|---|---|---|---|
| (I-1) | [structure] | 100 | 100 |
| (I-8) | [structure] | 100 | 99 |
| (I-11) | [structure] | 100 | 100 |

TABLE C-continued
Venturia test (apple)/protective
| Active compound | | Application rate of active compound in g/ha | % efficacy |
|---|---|---|---|
| (I-20) | 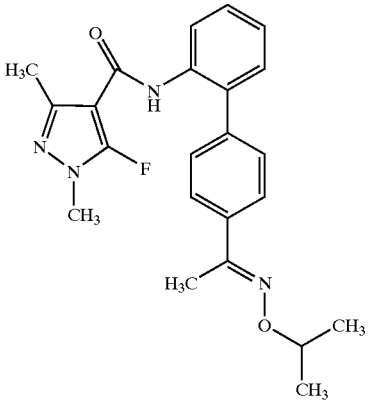 | 100 | 100 |
| (I-22) | 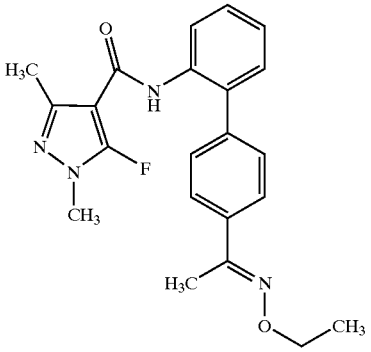 | 100 | 100 |
| (I-23) | 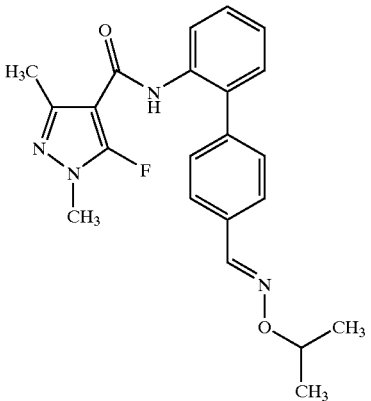 | 100 | 100 |

TABLE C-continued

Venturia test (apple)/protective

| Active compound | Application rate of active compound in g/ha | % efficacy |
|---|---|---|
| (I-26) | 100 | 100 |
| (I-29) | 100 | 100 |
| (I-37) | 100 | 100 |
| (I-39) | 100 | 100 |

TABLE C-continued

Venturia test (apple)/protective

| Active compound | | Application rate of active compound in g/ha | % efficacy |
|---|---|---|---|
| (I-46) | [structure: biphenyl with chloro and methoxyimino-methyl substituents, linked via amide to N-methyl-3-methyl-5-fluoropyrazole-4-carboxamide] | 100 | 100 |
| (I-47) | [structure: biphenyl with methyl and methoxyimino-methyl substituents, linked via amide to N-methyl-3-methyl-5-fluoropyrazole-4-carboxamide] | 100 | 100 |
| (I-50) | [structure: biphenyl with chloro, methyl, and methoxyimino-methyl substituents, linked via amide to N-methyl-3-methyl-5-fluoropyrazole-4-carboxamide] | 100 | 100 |

Example D

*Puccinia* Test (Wheat)/Protective

| | |
|---|---|
| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of approximately 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE D

Puccinia test (wheat)/protective

| Active compound | | Application rate of active compound in g/ha | % efficacy |
|---|---|---|---|
| (I-1) | [structure] | 250 | 100 |
| (I-3) | [structure] | 250 | 100 |
| (I-9) | [structure] | 250 | 100 |

TABLE D-continued

Puccinia test (wheat)/protective

| Active compound | Application rate of active compound in g/ha | % efficacy |
|---|---|---|
| (I-20) | 250 | 100 |
| (I-22) | 250 | 100 |
| (I-26) | 250 | 100 |

Example E
*Alternaria* Test (Tomato)/Protective

| Solvent: | 49 parts by weight of N,N-dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and then remain at 100% rel. humidity and 20° C. for 24 h. The plants then remain at 96% rel. atmospheric humidity and a temperature of 20° C.

Evaluation is carried out 7 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE E

Alternaria test (tomato)/protective

| Active compound | Application rate of active compound in g/ha | % efficacy |
|---|---|---|
| (I-1) | 750 | 95 |
| (I-2) | 750 | 90 |
| (I-4) | 750 | 90 |
| (I-5) | 750 | 90 |

TABLE E-continued

Alternaria test (tomato)/protective

| Active compound | | Application rate of active compound in g/ha | % efficacy |
|---|---|---|---|
| (I-7) | 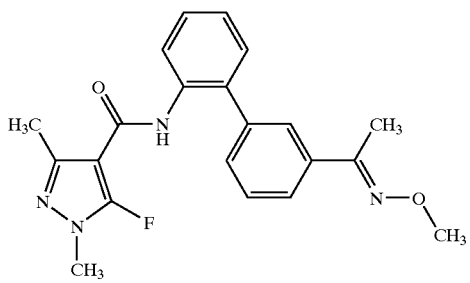 | 750 | 100 |

Example F
Inhibition Test on Giant Colonies of Basidiomycetes

Mycelium sections were removed from colonies of *Gloeophyllum trabeum, Coniophora puteana, Poria placenta, Lentinus tigrinus* and *Coriolus versicolor* and incubated on an agar medium containing malt extract peptone at 26° C. The inhibition of hyphal growth on active-compound-containing media was compared with the longitudinal growth on media without an addition of active compound and rated as per cent inhibition.

In this test, for example, the following compounds according to the invention of the Preparation Examples exhibit good activity:

TABLE F

Inhibition test on giant colonies of Basidiomycetes

| Active compound | | Application rate of active compound in ppm | % efficacy |
|---|---|---|---|
| (I-1) | 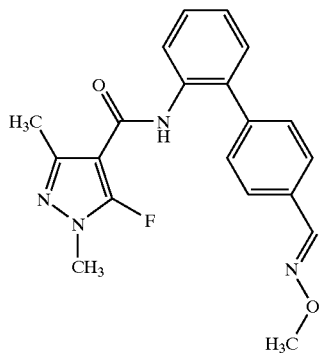 | 6 | 100 |
| (I-3) | 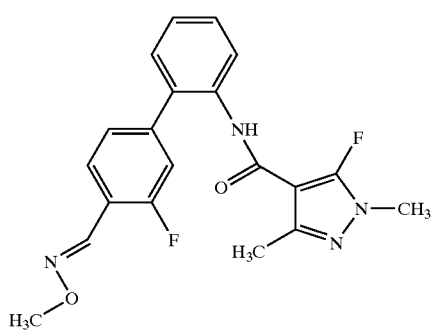 | 6 | 100 |

TABLE F-continued

Inhibition test on giant colonies of Basidiomycetes

| Active compound | Application rate of active compound in ppm | % efficacy |
|---|---|---|
| (I-4) | 6 | 100 |
| (I-9) | 6 | 100 |

What is claimed is:

1. A pyrazolylbiphenylcarboxamide of the formula (I-b)

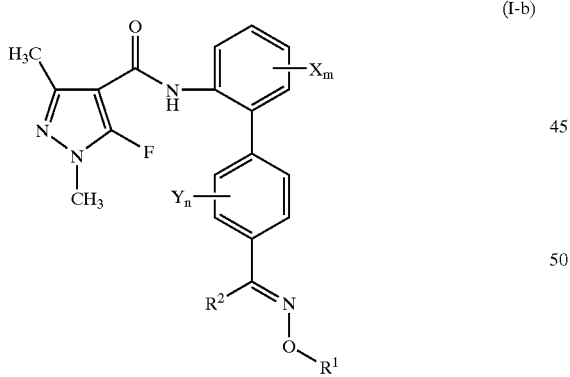

(I-b)

wherein
$R^1$ represents hydrogen, $C_1$–$C_6$-alkyl, or $C_1$–$C_6$-halogenoalkyl,
$R^2$ represents hydrogen or $C_1$–$C_6$-alkyl,
X represents halogen, nitro, cyano, hydroxyl, carboxyl, $C_1$–$C_8$-alkyl, $C_1$–$C_6$-halogenoalkyl having 1 to 5 halogen atoms, $C_1$–$C_8$-alkoxy, $C_1$–$C_8$-halogeno-alkoxy having 1 to 5 halogen atoms, $C_1$–$C_8$-alkylthio, $C_1$–$C_6$-halogenoalkylthio having 1 to 5 halogen atoms, $C_2$–$C_8$-alkenyloxy, $C_2$–$C_8$-alkinyloxy, $C_3$–$C_8$-cycloalkyl, $C_1$–$C_8$-alkoxycarbonyl or represents —C($R^2$)=N—$OR^1$, m represents integers from 0 to 3, where X represents identical or different radicals if m represents 2 or 3,
Y represents halogen, nitro, cyano, hydroxyl, carboxyl, $C_1$–$C_8$-alkyl, $C_1$–$C_6$-halogenoalkyl having 1 to 5 halogen atoms, $C_1$–$C_8$-alkoxy, $C_1$–$C_6$-halogenoalkoxy having 1 to 5 halogen atoms, $C_2$–$C_8$-alkylthio, $C_1$–$C_6$-halogenoalkylthio having 1 to 5 halogen atoms, $C_2$–$C_8$-alkenyloxy, $C_2$–$C_8$-alkinyloxy, $C_3$–$C_8$-cycloalkyl, $C_1$–$C_8$-alkoxycarbonyl or $C_1$–$C_6$-alkoximino-$C_1$–$C_6$-alkyl and
n represents integers from 0 to 4, where Y represents identical or different radicals if n represents 2, 3 or 4.

2. The pyrazolylbiphenylcarboxamide of the formula (I-b) according to claim 1 wherein
$R^1$ represents hydrogen, $C_1$–$C_4$-alkyl, or $C_1$–$C_2$-halogenoalkyl having 1 to 5 fluorine, chlorine and/or bromine atoms,
$R^2$ represents hydrogen or $C_1$–$C_4$-alkyl,
X represents fluorine, chlorine, bromine, nitro, cyano, hydroxyl, carboxyl, $C_1$–$C_6$-alkyl, $C_1$–$C_2$-halogenoalkyl having 1 to 5 fluorine, chlorine and/or bromine atoms, $C_1$–$C_6$-alkoxy, $C_1$–$C_2$-halogenoalkoxy having 1 to 5 fluorine, chlorine and/or bromine atoms, $C_1$–$C_6$-alkylthio, $C_1$–$C_2$-halogenoalkylthio having 1 to 5 fluorine, chlorine and/or bromine atoms, $C_2$–$C_6$-alkenyloxy, $C_2$–$C_5$-alkinyloxy, $C_3$–$C_7$-cycloalkyl, $C_1$–$C_4$-alkoxycarbonyl or represents —C($R^2$)=N—$OR^1$,
m represents integers from 0 to 3, where X represents identical or different radicals if m represents 2 or 3, Y represents fluorine, chlorine, bromine, nitro, cyano, hydroxyl, carboxyl, $C_1$–$C_6$-alkyl, $C_1$–$C_2$-halogenoalkyl having 1 to 5 fluorine, chlorine and/or bromine atoms, $C_1$–$C_6$-alkoxy, $C_1$–$C_2$-halogenoalkoxy having 1 to 5 fluorine, chlorine and/or bromine atoms, $C_1$–$C_6$-alkylthio, $C_1$–$C_2$-halogenoalkylthio having 1 to 5 fluorine, chlorine and/or bromine atoms, $C_2$–$C_6$-alkenyloxy, $C_2$–$C_6$-alkinyloxy, $C_3$–$C_7$-cycloalkyl, $C_1$–$C_4$-alkoxycarbonyl or $C_1$–$C_4$-alkoximino-$C_1$–$C_4$-alkyl, and n represents integers from 0 to 3, where Y represents identical or different radicals if n represents 2 or 3.

3. The pyrazolylbiphenylcarboxamide of the formula (I-b) according to claim 1 wherein $R^1$ represents hydrogen, methyl, ethyl, n-propyl, i-propyl, n-butyl, i-butyl, s-butyl, t-butyl, or 2-chloroethyl, $R^2$ represents hydrogen, methyl, ethyl, n-propyl, i-propyl or n-butyl, X represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, methylthio, trifluoromethylthio, difluorochloromethylthio, allyloxy, propargyloxy, cyclopropyl, cyclopentyl, cyclohexyl, cycloheptyl, methoxycarbonyl, ethoxycarbonyl or represents —C($R^2$)=N—O$R^1$, m represents integers from 0 to 2, where X represents identical or different radicals if m represents 2, Y represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, methylthio, trifluoromethylthio, difluorochloromethylthio, allyloxy, propargyloxy, cyclopropyl, cyclopentyl, cyclohexyl, cycloheptyl, methoxycarbonyl, ethoxycarbonyl or methoximinomethyl, and n represents integers from 0 to 2, where Y represents identical or different radicals if n represents 2.

4. A process for preparing a pyrazolylbiphenylcarboxamide of the formula (I-b) according to claim 1, comprising reacting a carboxylic acid derivative of the formula (II)

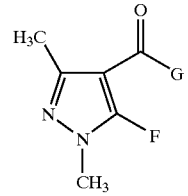

(II)

wherein

G represents halogen, hydroxyl or $C_1$–$C_6$-alkoxy, with an aniline derivative of the formula (III)

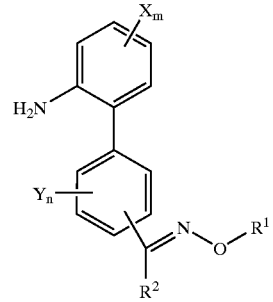

(III)

wherein $R^1$, $R^2$, X, m, Y and n are each as defined in claim 1, optionally in the presence of a catalyst, optionally in the presence of an acid binder and optionally in the presence of a diluent.

5. A composition for controlling undesirable fungi, comprising one or more pyrazolylbiphenylcarboxamide of the formula (I-b) according to claim 1, and one or more extenders and/or surfaactants.

6. A method for controlling undesirable fungi, comprising applying an effective amount of a pyrazolylbiphenylcarboxamide of the formula (I-b) according to claim 1 to the fungi and/or their habitat.

* * * * *